US012623757B2

(12) United States Patent
Qiu

(10) Patent No.: US 12,623,757 B2
(45) Date of Patent: May 12, 2026

(54) VEHICLE-CARRIED FIRST AID KIT

(71) Applicant: Ningbo Huazhou Optoelectronic Technology Co., Ltd., Ningbo City (CN)

(72) Inventor: Enyuan Qiu, Ningbo City (CN)

(73) Assignee: Ningbo Huazhou Optoelectronic Technology Co., Ltd., Ningbo City (CN)

( * ) Notice: Subject to any disclaimer, the term of this patent is extended or adjusted under 35 U.S.C. 154(b) by 741 days.

(21) Appl. No.: 17/978,237

(22) Filed: Nov. 1, 2022

(65) Prior Publication Data

US 2023/0312064 A1     Oct. 5, 2023

(30) Foreign Application Priority Data

Mar. 14, 2022    (CN) .......................... 202210246625.0

(51) Int. Cl.
B63C 9/00 (2006.01)
A61F 9/02 (2006.01)
(Continued)

(52) U.S. Cl.
CPC ................ B63C 9/00 (2013.01); A61F 9/029 (2013.01); B60R 11/06 (2013.01); B60R 21/02 (2013.01); B60R 2021/0016 (2013.01)

(58) Field of Classification Search
CPC .. B63C 9/00; B63C 9/022; B63C 9/06; B63C 11/18; B63C 11/22; A61F 9/029; A61F 17/00; B60R 11/06; B60R 11/14; B60R 21/02; B60R 2021/0016; A62B 3/005; A62B 7/00; A62B 7/04; B65D 51/1683
See application file for complete search history.

(56) References Cited

U.S. PATENT DOCUMENTS 4,479,520 A * 10/1984 Holben ................... F17C 13/04
                                                                285/104
4,676,236 A * 6/1987 Piorkowski ............ A62B 18/04
                                                                128/201.25
(Continued)

FOREIGN PATENT DOCUMENTS

CN        204428653 U * 7/2015
CN        109237292 A * 1/2019 ............... F17C 1/00
(Continued)

*Primary Examiner* — Timothy A Stanis
*Assistant Examiner* — Matthew R Moon
(74) *Attorney, Agent, or Firm* — Getech Law LLC; Jun Ye

(57) ABSTRACT

A vehicle-carried first aid kit includes a first aid kit body, and the first aid kit body is internally provided with a portable respirator, oxygen inhalation goggles, a floating rope, a first aid bracelet, a military shovel, cut-resistant gloves, a multifunctional tool bag and a medical supply bag. The portable respirator includes a main valve body and a gas cylinder. A pressure relief diaphragm is mounted inside the main valve body. A pressure relief valve is disposed inside the main valve body. The main valve body is provided with an inflation opening. An exhaust opening is disposed at the bottom of the main valve body. The oxygen inhalation goggles include a goggle frame fitted with lenses and a flexible skirt edge disposed around the goggle frame to form a respiratory chamber. An inlet gas tube is inserted into the flexible skirt edge.

9 Claims, 9 Drawing Sheets

(51) Int. Cl.
  *B60R 11/06*   (2006.01)
  *B60R 21/02*   (2006.01)
  *B60R 21/00*   (2006.01)

(56)     References Cited

U.S. PATENT DOCUMENTS

| | | | | |
|---|---|---|---|---|
| 5,704,073 | A | * | 1/1998 | Sword ................ A41D 13/1176 |
| | | | | 2/427 |
| 5,778,875 | A | * | 7/1998 | Morgan ............. G05D 16/0663 |
| | | | | 128/205.24 |
| 2003/0217774 | A1 | * | 11/2003 | Markham ............... F16K 1/306 |
| | | | | 137/613 |
| 2005/0000515 | A1 | * | 1/2005 | Pokras ................... B63C 11/12 |
| | | | | 128/201.27 |
| 2009/0184119 | A1 | * | 7/2009 | Takanohashi ...... B65D 51/1683 |
| | | | | 220/212 |
| 2011/0130636 | A1 | * | 6/2011 | Daniel ................... G16H 40/20 |
| | | | | 709/201 |
| 2013/0152262 | A1 | * | 6/2013 | Bedetti ........... A41D 19/01529 |
| | | | | 2/16 |

FOREIGN PATENT DOCUMENTS

| | | | | | |
|---|---|---|---|---|---|
| CN | 109969117 | A | * | 7/2019 | ............ A62B 3/005 |
| CN | 210139953 | U | * | 3/2020 | |
| CN | 213963965 | U | * | 8/2021 | |
| JP | S63108894 | U | * | 7/1988 | |
| KR | 20120124716 | A | * | 11/2012 | .............. A62B 7/04 |
| KR | 20220030488 | A | * | 3/2022 | .............. A62B 7/02 |

* cited by examiner

A-A

VEHICLE-CARRIED FIRST AID KIT

This application is based upon and claims priority to Chinese Patent Application No. 202210246625.0, filed on Mar. 14, 2022, the entire contents of which are incorporated herein by reference.

TECHNICAL FIELD

The present invention relates to the field of life-saving articles and in particular to a vehicle-carried first aid kit.

BACKGROUND

Vehicle-carried first aid kit is a bag provided with medical first aid equipment and medications on a vehicle, which can be used to carry out self-rescue upon occurrence of deaths or injuries caused by traffic accidents and therefore can be regarded as one of major approaches to effectively reduce the death toll of traffic accidents. But, the vehicle-carried first aid kits on the current market are only applicable to the problems of minor abrasions or bleeding arising from traffic accidents and cannot cope with a severe circumstance of a vehicle running across water, bringing limitations to use of the vehicle-carried first aid kit. Therefore, it is urgent to need a vehicle-carried first aid kit which can not only handle the common problems of abrasions or bleeding but also carry out emergency oxygen inhalation for a drowning person in time during an accident of a vehicle running across water.

SUMMARY

In order to address the above technical problems, the present invention provides a vehicle-carried first aid kit which is provided with a portable respirator and oxygen inhalation goggles to carry out emergency respiration treatment for a drowning person in different conditions.

The present invention adopts the following technical solution. A vehicle-carried first aid kit is provided, which comprises a first aid kit body. The first aid kit body is internally provided with a portable respirator, oxygen inhalation goggles, a floating rope, a first aid bracelet, a military shovel, cut-resistant gloves, a multifunctional tool bag and a medical supply bag. The portable respirator comprises a main valve body and a gas cylinder. A pressure relief diaphragm is mounted inside the main valve body. An outer side of the pressure relief diaphragm is in communication with the atmospheric environment and an inner side of the pressure relief diaphragm forms a low-pressure compartment with an inner wall of the main valve body. The low-pressure compartment is in communication with a gas outlet of a gas outlet end of the gas cylinder through an inlet gas channel. A pressure relief valve is disposed inside the main valve body. A pressure relief channel in communication with the inlet gas channel and the low-pressure compartment is disposed in a valve body of the pressure relief valve. A pressure relief opening is disposed on the valve body of the pressure relief valve. The pressure relief diaphragm is linked with the pressure relief valve through a pressing mechanism. The main valve body is provided with an inflation opening in communication with the inlet gas channel and a mouthpiece interface in communication with the low-pressure compartment. An exhaust opening in communication with the low-pressure compartment is disposed at the bottom of the main valve body, and the exhaust opening is provided with a one-way exhaust diaphragm.

The oxygen inhalation goggles comprise a goggle frame fitted with lenses and a flexible skirt edge disposed around the goggle frame to form a respiratory chamber. An inlet gas tube is inserted into the flexible skirt edge. One end of the inlet gas tube communicates with the respiratory chamber and extends to a nose part, where the end is provided with nose plugs for ease of inhalation; and the other end of the inlet gas tube is connected with a portable oxygen cylinder. The goggle frame is provided with a binding strap fixed to a head part, and the binding strap is provided with an elastic strap for detachably mounting the portable oxygen cylinder to the binding strap.

With the above structure, the present invention has the following advantages: the floating rope, the first aid bracelet, the military shovel, the cut-resistant gloves, a multifunctional tool bag and a medical supply bag can satisfy regular on-water emergency requirements and the portable respirator and the oxygen inhalation goggles can be used to carry out emergency respiration rescue for a drowning person. Especially in an emergency of hypoxia, the portable respirator and the oxygen inhalation goggles can be quickly applied due to their portability and light weight.

When inhalation is performed using the portable respirator, the pressure relief diaphragm in the low-pressure compartment deforms downwardly to push the pressing mechanism to press down, thus pushing a piston of the pressure relief valve to run downwardly. In this way, the pressure relief channel is communicated with the inlet gas channel to enable gas in the inlet gas channel to enter the low-pressure compartment for inhalation by a user. When exhalation is performed, the pressure relief diaphragm deforms upwardly to loosen the pressing mechanism, and the piston of the pressure relief valve is driven under a restoring force of an elastic piece to disconnect the pressure relief channel and the inlet gas channel such that the gas will not enter the pressure relief channel. In this case, gas exhaled by the user pushes open the exhaust diaphragm of the exhaust opening for discharge. Hence, the portable respirator has the advantages of simple structure, ease of implementation, portability and ease of use.

The goggle frame of the oxygen inhalation goggles can be put on a face part stably and sealingly through the flexible skirt edge. One end of the inlet gas tube penetrates through the respiratory chamber formed by the flexible skirt edge and communicates with the respiratory chamber whereas the other end of the inlet gas tube is connected with the portable oxygen cylinder to perform continuous oxygen supply, helping an underwater rescue person to stay underwater for long without floating up and down to carry out alternating breathing. The portable oxygen cylinder is fixed onto the binding strap through the elastic strap, that is, the portable oxygen cylinder is directly fixed on the elastic strap without requiring a hand to hold the portable oxygen cylinder, thus achieving the purpose of better portability. In this case, the underwater rescue person can carry out rescue with free hands, so as to increase the rescue success rate. Further, the oxygen inhalation goggles may also be used for an emergency person having inconvenience in using hands because it is only required to sleeve the elastic strap on the portable oxygen cylinder, bringing conveniences and ease.

Preferably, the top of the main valve body is provided with a detachable end cover with an air vent. The outer side of the pressure relief diaphragm is in communication with the atmospheric environment through the air vent. If the top is sealed, a space between the top and the pressure relief diaphragm can be fixed to prevent the pressure relief diaphragm from deforming. Therefore, the end cover with the air vent on the top can, on one hand, fix the circumference of the pressure relief diaphragm, on the other hand, prevent the product from being improperly used to cause the pressure relief diaphragm to excessively expand beyond an expansion limit of material, thereby avoiding damage to the product.

The pressing mechanism includes a movable lever and a push rod. One end of the movable lever is abutted against the pressure relief diaphragm and the other end of the movable lever is connected with the piston of the pressure relief valve through the push rod. One end of the piston is abutted inside the valve body through the elastic piece, and the other end of the piston is abutted against an outlet of the pressure relief channel through a plug. The pressure relief diaphragm deforms to press or loosen the pressing mechanism which then drives the piston to move up and down, thus opening or closing the outlet of the pressure relief channel by the piston to supply or stop supplying gas.

Preferably, a gas inlet end of the inlet gas channel is connected with the gas outlet end of the gas cylinder through a connection piece. The connection piece includes a first connection portion and a second connection portion. Protruding blocks matching a flare of the gas outlet end of the gas cylinder is disposed on an inner wall of the first connection portion. An external hooping piece is sleeved on an outer wall of the first connection portion. The external hooping piece tightly embraces the first connection portion onto the gas outlet end of the gas cylinder. The second connection portion is slidably connected with an input end of the inlet gas channel. A first limiting groove in communication with the inlet gas channel is opened at the center of the input end of the inlet gas channel. The gas outlet of the gas outlet end of the gas cylinder extends into the first limiting groove. A gap is reserved between a bottom surface of the first limiting groove and an end surface of the gas outlet. When the second connection portion slides toward the inlet gas channel, the bottom surface of the first limiting groove is abutted and pressed against the end surface of the gas outlet, so as to open the gas outlet. When the second connection portion slides away from the inlet gas channel, the bottom surface of the first limiting groove goes away from the end surface of the gas outlet of the gas cylinder, so as to close the gas outlet. Thus, with the simple structure, the gas cylinder and the first connection portion are connected securely where the connection is easy to operate. The second connection portion is slidably connected with an end of the inlet gas channel extending from the main valve body. The first limiting groove is disposed at the end of the inlet gas channel and the gas outlet of the gas outlet end of the gas cylinder extends into the first limiting groove. A gap is reserved between the end surface of the gas outlet and the bottom surface of the first limiting groove. The gas outlet can stretchably move along the gap such that the end surface of the gas outlet can abut against or go away from the bottom surface of the first limiting groove. In other words, when the second connection portion slides upwardly along the inlet gas channel, the second connection portion brings the gas cylinder to slide upwardly and the end surface of the gas outlet abuts against the bottom surface of the first limiting groove, that is, the bottom surface of the first limiting groove presses the end surface of the gas outlet. At this time, the gas outlet of the gas cylinder is in an opened state. When the second connection portion slides downwardly along the inlet gas channel, the second connection portion brings the gas cylinder to slide downwardly and the end surface of the gas outlet goes away from the bottom surface of the first limiting groove, and thus the gas outlet is reset. At this time, the gas outlet of the gas cylinder is in a closed state. Therefore, the connection piece has the advantages of simple structure, ease of implementation, and secure and stable connection while having the effect of releasing or stopping releasing gas of the gas cylinder, bringing practical conveniences.

Preferably, a through hole is opened in the flexible skirt edge and a rubber plug is mounted in the through hole. An end of the inlet gas tube penetrates through the rubber plug to communicate with the respiratory chamber and extend to the nose part. With the rubber plug, the inlet gas tube can be stably fixed and sealing between the inlet gas tube and the through hole can be guaranteed. A part of the inlet gas tube passing through the rubber plug is a straight-line section to ensure the inlet gas tube can be quickly and easily inserted through the rubber plug without using any auxiliary tool and sealing between the inlet gas tube and the rubber plug can be achieved.

Preferably, an end of the inlet gas tube is rotatably connected with an extension portion on which the nose plugs are fixed, such that the nose plugs can be rotated along with the extension portion and thus can be adjusted to a different angle to adapt to the nose position.

Preferably, both ends of the elastic strap are connected with the binding strap to form a ring shape and the portable oxygen cylinder is sleeved into the ring-shaped elastic strap such that the portable oxygen cylinder is tightly hooped by shrinkage of the elastic strap.

Preferably, the elastic strap is located in a middle position of a length direction of the binding strap and the portable oxygen cylinder is horizontally fixed. Thus, the portable oxygen cylinder is located behind the head part. A gas discharge port of the portable oxygen cylinder is disposed at the same side as the through hole of the flexible skirt edge, such that the inlet gas tube connecting the gas discharge port of the portable oxygen cylinder can be horizontally disposed in a shortest length to ensure the inlet gas tube can supply gas normally without any leakage, thus minimizing the potential safety hazards.

Preferably, a width size of the elastic strap is greater than or equal to ¼ of a body length of the portable oxygen cylinder, such that the portable oxygen cylinder can be stably fixed to the binding strap through the elastic strap, thus preventing a head and a tail of the portable oxygen cylinder from floating up and down.

Preferably, the multi-functional tool bag includes a working lamp, a safety hammer, a flashlight, a headlamp and an emergency urine bag. The medical supply bag includes gauzes, adhesive bandages, iodine cotton swabs and adhesive tapes. The two bags can be applied to regular emergency rescues to cope with different emergency conditions.

BRIEF DESCRIPTIONS OF THE DRAWINGS

Numerals of the drawings are described as follows: 1. main valve body, 2. gas cylinder, 2-1. gas outlet, 2-2. flare, 3. inlet gas channel, 3-1. first limiting groove, 4. connection piece, 4-1. first connection portion, 4-2. second connection portion, 4-3. protruding block, 4-4. external hooping piece, 4-5. closing portion, 4-6. damping protruding ridge, 4-7. connection block, 5. breathing mouthpiece;

6. pressure relief diaphragm, 7. low-pressure compartment, 8. pressure relief valve, 8-1. pressure relief channel, 8-2. valve seat, 8-3. pressure relief opening, 8-4. piston, 8-5. elastic piece, 8-6. plug, 9. pressing mechanism, 9-1. movable lever, 9-2. push rod, 10. end cover, 11. exhaust opening, 12. inflation opening, 13. mouthpiece interface, 14. one-way exhaust diaphragm;

15. goggle frame, 16. lens, 17. flexible skirt edge, 18. respiratory chamber, 19. inlet gas tube, 20. nose plug, 21. portable oxygen cylinder, 22. binding strap, 23. elastic strap, 24. through hole, 25. rubber plug, 26. extension portion, 27. regulator, 28. military shovel, 28-1. handle, 28-2. shovel, 29. first aid bracelet, 29-1. compressed gas cylinder, 29.2. wristband, 29-3. foldable airbag, 29-4. control valve;

30. first connection piece, 31. third connection portion, 32. fourth connection portion, 33. fixing portion, 34. first protrusion, 35. first flare, 36. first external hooping piece, 37. limiting port, 38. pressing portion, 39. outlet gas channel, 40. second limiting groove.

DETAILED DESCRIPTIONS OF EMBODIMENTS

The present invention will be further described below in combination with accompanying drawings and specific embodiments.

Figure 1:
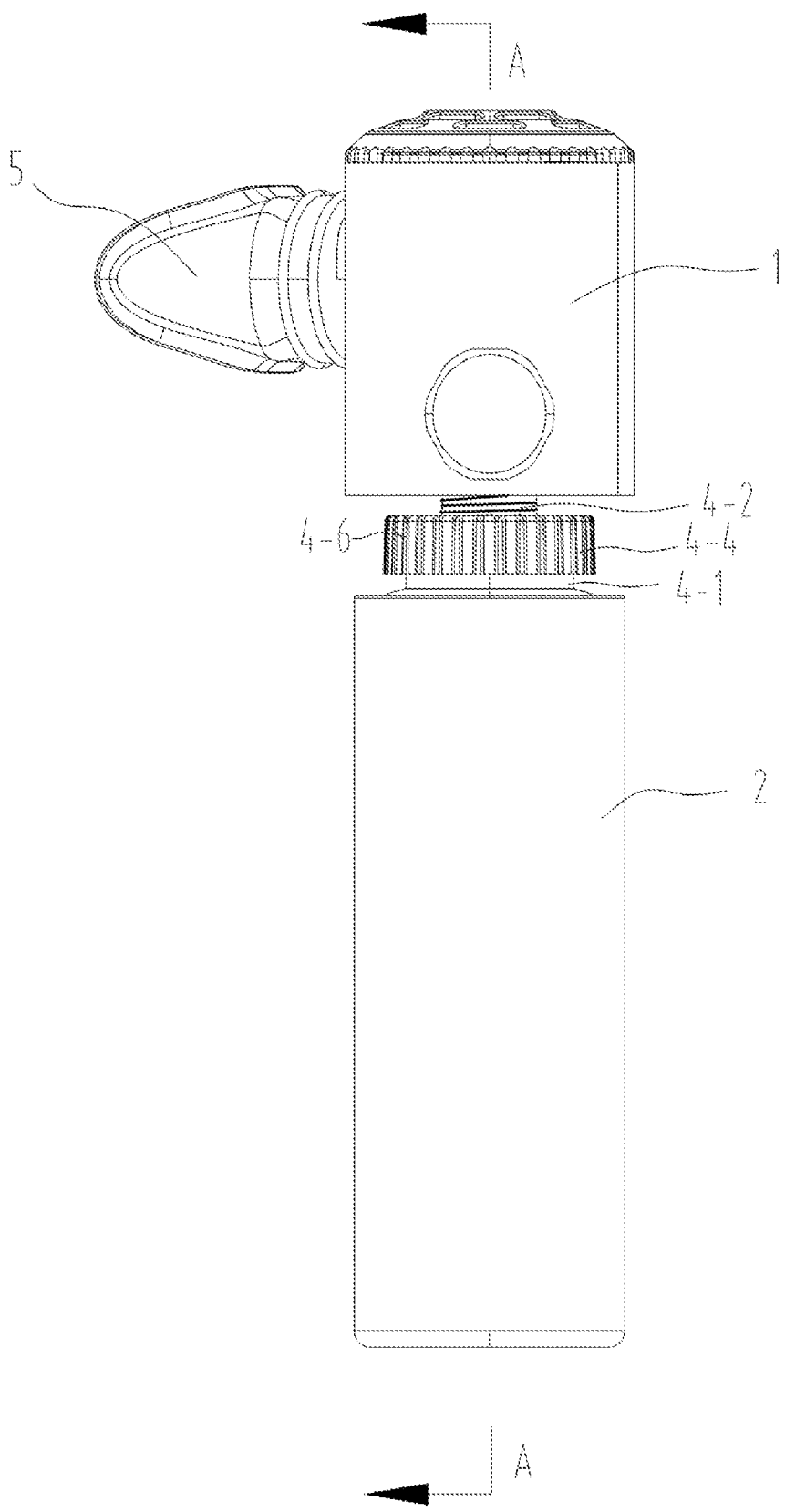
FIG. 1 is an entire front view of a portable respirator according to the present invention.
Figure 2:
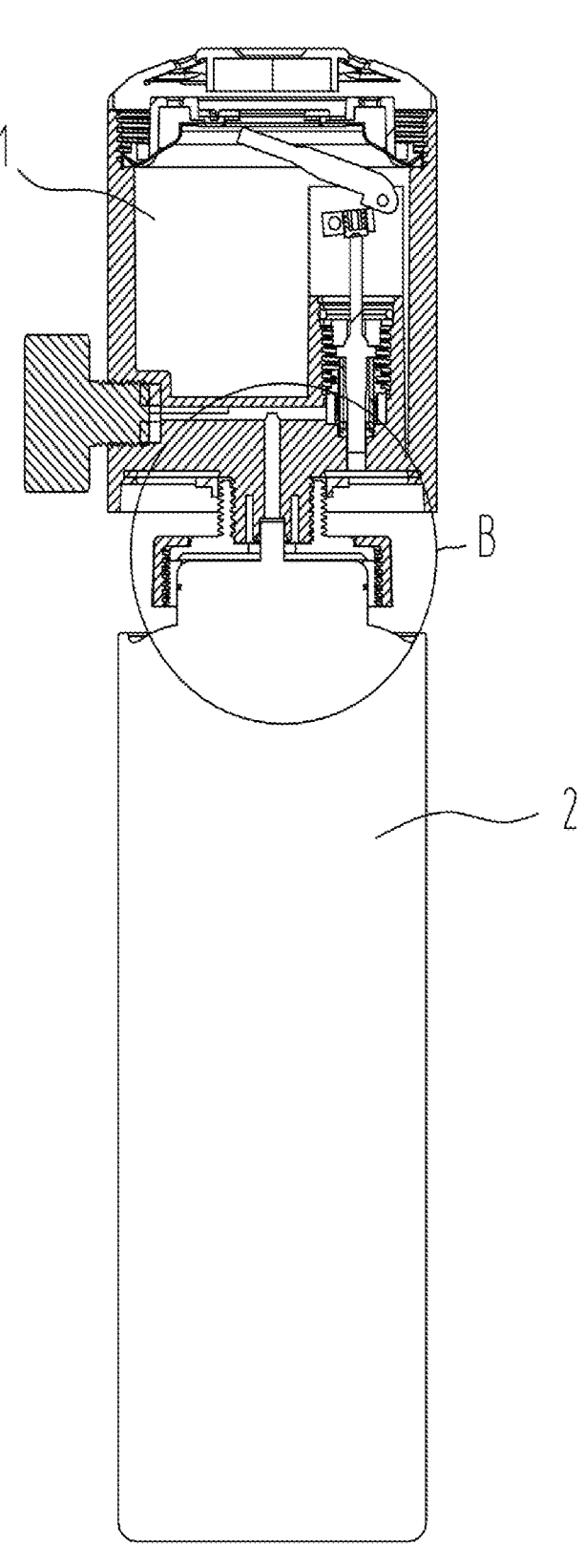
FIG. 2 is a view taken along A-A in FIG. 1.

The present invention provides a vehicle-carried first aid kit. As shown in FIGS. 1 and 2, the vehicle-carried first aid kit comprises a portable respirator, oxygen inhalation goggles, a floating rope, a first aid bracelet 29, a military shovel 28, cut-resistant gloves, a multifunctional tool bag and a medical supply bag.

Figure 3:
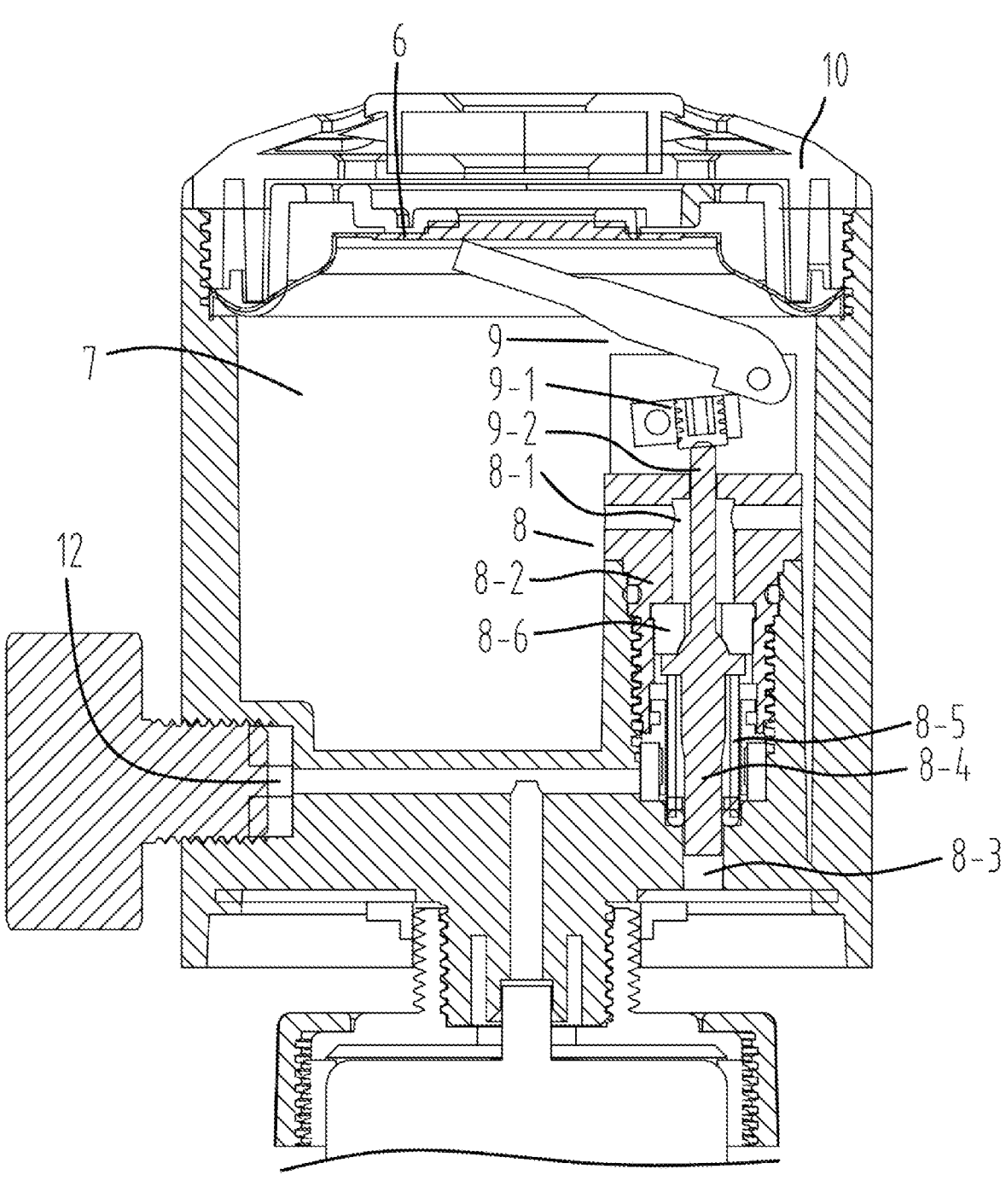
FIG. 3 is a sectional view of a main valve body of a portable respirator according to the present invention.

The portable respirator comprises a main valve body 1 and a gas cylinder 2. In this embodiment, as shown in FIG. 3, a sealing pressure relief diaphragm 6 is mounted at top inside the main valve body 1. An outer side of the pressure relief diaphragm 6 is in communication with the atmospheric environment and an inner side of the pressure relief diaphragm 6 forms a low-pressure compartment 7 with an inner wall of the main valve body 1. The low-pressure compartment 7 is provided with an inlet gas channel 3 for communicating with a gas outlet end of the gas cylinder 2. Oxygen ejected from a gas outlet 2-1 of the gas outlet end of the gas cylinder 2 runs through the inlet gas channel 3 into the low-pressure compartment 7. A pressure relief valve 8 is disposed inside the main valve body 1. A pressure relief channel 8-1 is disposed on a valve seat 8-2 of the pressure relief valve 8. One end of the pressure relief channel 8-1 is in communication with the low-pressure compartment 7 and the other end of the pressure relief channel 8-1 is in communication with the inlet gas channel 3. A pressure relief opening 8-3 is further disposed in the pressure relief channel 8-1. A pressing mechanism 9 is connected with a top end of a piston 8-4 of the pressure relief valve 8. One end of the pressing mechanism 9 is abutted against the pressure relief diaphragm 6 and the other end of the pressing mechanism 9 is abutted against an opening between the pressure relief channel 8-1 and the inlet gas channel 3. In this embodiment, the pressing mechanism 9 comprises a movable lever 9-1 and a push rod 9-2. One end of the movable lever 9-1 is abutted against the pressure relief diaphragm 6 and the other end of the movable lever 9-1 is connected with the piston 8-4 of the pressure relief valve 8 through the push rod 9-2. One end of the piston 8-4 is abutted inside the valve seat 8-2 through an elastic piece 8-5, and the other end of the piston 8-4 is abutted against an outlet of the pressure relief channel 8-1 through a plug 8-6. The pressure relief opening 8-3 is used to prevent the piston 8-5 from compressing gas. Under the compression and restoring forces of the elastic piece 8-5, the piston 8-4 moves up and down along the pressure relief channel 8-1, that is, by using the piston 8-4 as a switch to connect and disconnect the pressure relief channel 8-1 and the inlet gas channel 3, high pressure gas in the inlet gas channel 3, after being depressurized, enters the low-pressure compartment 7, and the low-pressure compartment 7 communicates with a mouthpiece interface 13 provided with a mouthpiece for breathing.

Figure 5:
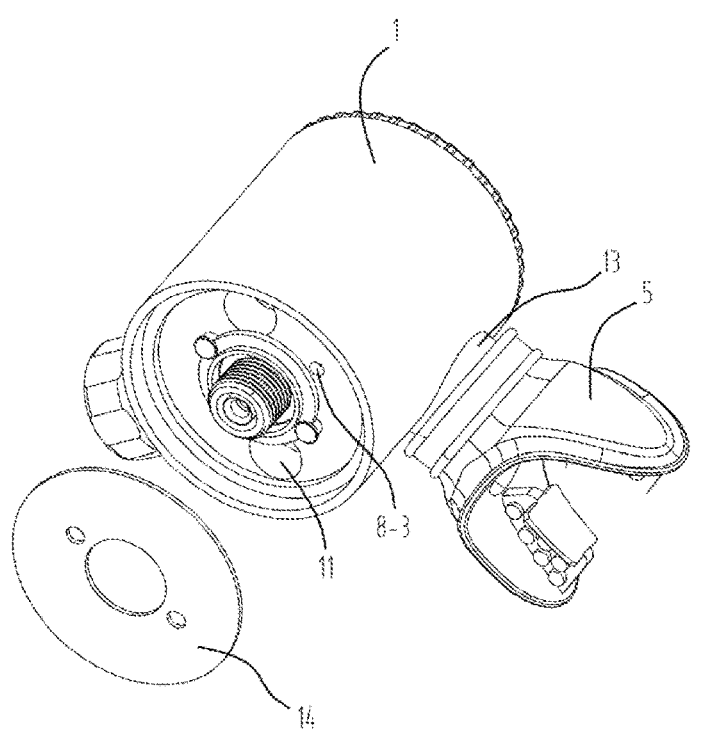
FIG. 5 is an exploded view of a one-way exhaust diaphragm and a position of an exhaust opening according to the present invention.

The main valve body 1 is provided with an inflation opening 12 in communication with the inlet gas channel 3. An inflation valve is disposed on the inflation opening 12. After the inflation valve is connected to an external inflation source and turned on, oxygen coming from the external inflation source enters the gas outlet 2-1 of the gas cylinder 2 through the inlet gas channel 3 so as to inflate the gas cylinder 2. An exhaust opening 11 in communication with the low-pressure compartment 7 is disposed at the bottom of the main valve body 1, and the exhaust opening 11 is provided with a one-way exhaust diaphragm. As shown in FIG. 5, the one-way exhaust diaphragm is sleeved on and fixed with a fastener to an input end of the inlet gas channel 3. The one-way exhaust diaphragm is usually made of rubber. The one-way exhaust diaphragm is covered on and closely attached to the exhaust opening 11 and the pressure relief opening 8-3, such that gas can only come out of the exhaust opening 11 and the pressure relief opening 8-3 but cannot enter from the external atmospheric environment, thus avoiding entry of water in an underwater environment.

The gas cylinder 2 is a common custom gas cylinder 2 on market. There is one circle of fare 2-2 horizontally out-turned on the gas outlet end of the gas cylinder 2.

Figure 4:
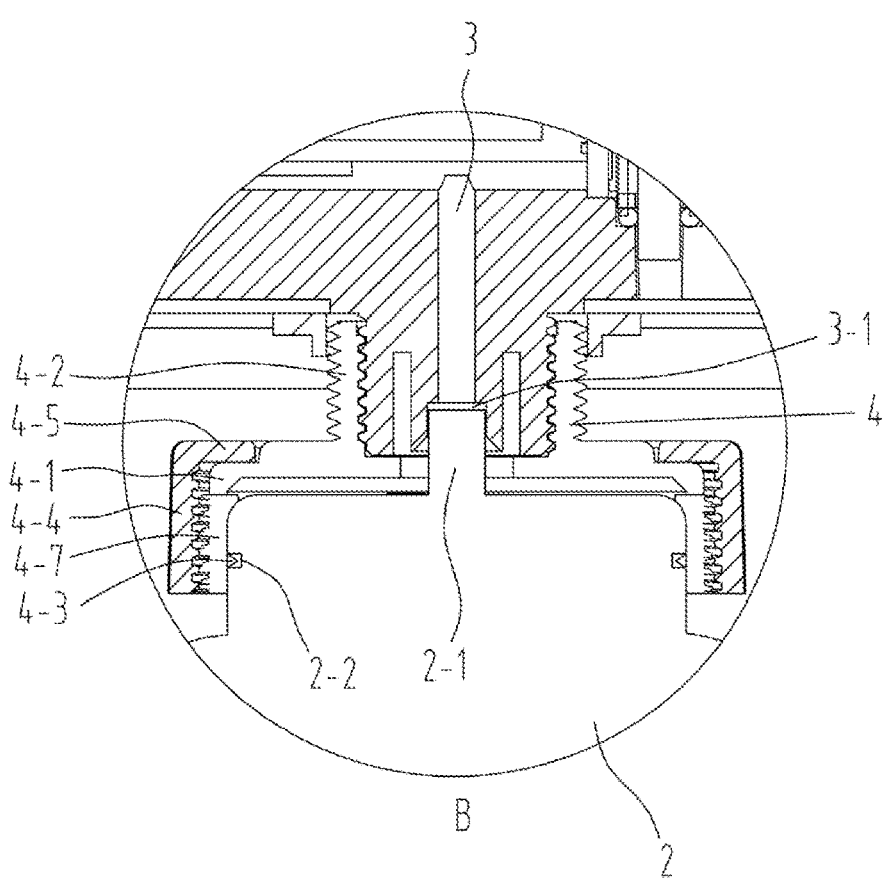
FIG. 4 is an enlarged view of a position B in FIG. 2.

The gas inlet end of the inlet gas channel 3 is connected with the gas outlet end of the gas cylinder 2 through a connection piece 4. The gas in the gas cylinder 2 enters the main valve body 1 through the inlet gas channel 3, and then the gas in the main valve body 1 enters a human body through a breathing mouthpiece 5. As shown in FIG. 4, the connection piece 4 comprises a first connection portion 4-1 and a second connection portion 4-2. The first connection portion 4-1 and the second connection portion 4-2 are integrally formed. Each of the first connection portion 4-1 and the second connection portion 4-2 is a cover structure with an opening.

The first connection portion 4-1 is sleeved on the gas outlet end of the gas cylinder 2, and protruding blocks 4-3 are disposed on an inner wall of the first connection portion 4-1. The protruding blocks 4-3 extend from the inner wall of the first connection portion 4-1 and are distributed like a ring. By pressing the first connection portion 4-1 to the gas outlet end of the gas cylinder 2, the protruding blocks 4-3 can be fitted below the flare 2-2 of the gas outlet end of the gas cylinder 2 to form axial limitation, and thus the first connection portion 4-1 is fitted to the gas outlet end of the gas cylinder 2.

An external hooping piece 4-4 shaped like a cover structure with an opening is sleeved on an outer wall of the first connection portion 4-1. Internal threads are disposed on an inner circumferential wall of the external hooping piece 4-4 and outer threads matching the inner threads of the external hooping piece 4-4 are disposed on the first connection portion 4-1. The external hooping piece 4-4 is connected to an outer circumferential wall of the first connection portion 4-1 by thread connection, that is, the external hooping piece 4-4 can move up and down along the outer circumferential wall of the first connection portion 4-1. In this way, the external hooping piece 4-4 tightly embraces the first connection portion 4-1 to the gas outlet end of the gas cylinder 2 and connection between the first connection portion 4-1 and the gas outlet end of the gas cylinder 2 is reinforced.

The input end of the inlet gas channel 3 extends from the main valve body 1 to form a connection end provided with external threads, and the second connection portion 4-2 is provided with internal threads matching the external threads. The slide connection between the second connection portion 4-2 and the inlet gas channel 3 is performed using thread connection, and the structure is simple, stable and easy to implement. It is noted that after a top end of the first connection portion 4-1 is connected with the inlet gas channel 3, a gap is reserved between the top end of the first connection portion 4-1 and an external surface of a root portion of the inlet gas channel 3 to adapt to up-down slide adjustment between the first connection portion 4-1 and the inlet gas channel 3.

A top end of the external hooping piece 4-4 extends to be above the first connection portion 4-1 and form a closing portion 4-5. The closing portion 4-5 and the first connection portion 4-1 are fitted together. When the external hooping piece 4-4 is sleeved on the first connection portion 4-1 and slid down to a lowest point, the closing portion 4-5 can be tightly pressed on an end surface of the first connection portion 4-1 to form limitation, preventing the external hooping piece 4-4 from continuing sliding down and separating from the first connection portion 4-1.

Damping protruding ridges 4-6 are disposed in a spacing on an outer circumferential wall of the external hooping piece 4-4 to facilitate manual rotation.

Furthermore, a part of the first connection portion 4-1 connecting the external hooping piece 4-4 is a plurality of connection blocks 4-7 distributed circumferentially. A gap is disposed between adjacent connection blocks 4-7 and a protruding block 4-3 is disposed on a surface of each connection block 4-7 facing toward the gas outlet end of the gas cylinder 2. The protruding blocks 4-3 on all connection blocks 4-7 are disposed at a same horizontal level. The plurality of connection blocks 4-7 are disposed in such a way that the plurality of connection blocks 4-7 can deform outwardly for buffering when the protruding blocks 4-3 of the first connection portion 4-1 are fitted into the flare 2-2 of the gas outlet end of the gas cylinder 2 along the outer wall of the gas outlet end of the gas cylinder 2. Thus, the mounting can be operated easily with less effort. The other side surface of the first connection portion 4-1 is provided with outer threads matching the inner threads of the external hooping piece 4-4, such that the external hooping piece 4-4 can be connected to the outer circumferential wall of the first connection portion 4-1 by thread connection.

A first limiting groove 3-1 in communication with the inlet gas channel 3 is opened at the center of the input end of the inlet gas channel 3, where the first limiting groove 3-1 has a greater diameter than the inlet gas channel 3. The gas outlet 2-1 of the gas outlet end of the gas cylinder 2 extends into the first limiting groove 3-1 such that the inlet gas channel 3 is communicated with the first limiting groove 3-1 and the gas outlet 2-1 of the gas outlet end of the gas cylinder 2. At this time, a gap is reserved between a bottom surface of the first limiting groove 3-1 and an end surface of the gas outlet 2-1. When the second connection portion 4-2 slides toward the inlet gas channel 3, the bottom surface of the first limiting groove 3-1 is abutted and pressed against the end surface of the gas outlet 2-1, so as to open the gas outlet 2-1. At this time, the gas coming from the gas outlet 2-1 of the gas cylinder 2 enters the inlet gas channel 3 through the first limiting groove 3-1 and then enters the main valve body 1 along the inlet gas channel 3. When the second connection portion 4-2 slides away from the inlet gas channel 3, the bottom surface of the first limiting groove 3-1 goes away from the end surface of the gas outlet 2-1 of the gas cylinder 2, that is, the gas outlet 2-1 of the gas cylinder 2 closes for release, so as to close the gas outlet 2-1. In one word, when the second connection portion 4-2 slides up and down along the input end of the inlet gas channel 3, the first limiting groove 3-1 of the input end of the inlet gas channel 3 presses against or goes away from the gas outlet 2-1 of the gas cylinder 2, thus opening and closing the gas outlet 2-1 of the gas cylinder 2. Since the second connection portion 4-2 and the input end of the inlet gas channel 3 are connected by threads, accurate rotation amount can be achieved so as to achieve accurate control on closing and opening of the gas outlet 2-1 of the gas cylinder 2.

The working principle of the portable respirator is as follows: the pressure relief diaphragm 6 is linked with the pressure relief valve 8 through the pressing mechanism 9; when inhalation is performed, a negative pressure state is formed in the low-pressure compartment 7, the pressure relief diaphragm 6 in the low-pressure compartment 7 deforms downwardly to push the pressing mechanism 9 to press down, thus pushing a piston 8-4 of the pressure relief valve 8 to run downwardly; in this way, the pressure relief channel 8-1 is communicated with the inlet gas channel 3 to enable gas in the inlet gas channel 3 to enter the low-pressure compartment 7 for inhalation by a user; when exhalation is performed, the pressure relief diaphragm 6 deforms upwardly to loosen the pressing mechanism 9, and the piston 8-4 of the pressure relief valve 8 is driven under a restoring force of an elastic piece 8-5 to disconnect the pressure relief channel 8-1 and the inlet gas channel 3 such that the gas will not enter the pressure relief channel 8-1; and thus, gas exhaled by the user pushes open the one-way exhaust diaphragm of the exhaust opening 11 for discharge.

In addition, the top of the main valve body of the portable respirator is provided with a detachable end cover 10 with an air vent. The outer side of the pressure relief diaphragm 6 is in communication with the atmospheric environment through the air vent. If the top is sealed, a space between the top and the pressure relief diaphragm 6 can be fixed to prevent the pressure relief diaphragm 6 from deforming. Therefore, the end cover 10 with the air vent on the top can, on one hand, fix the circumference of the pressure relief diaphragm 6, on the other hand, prevent the product from being improperly used to cause the pressure relief diaphragm 6 to excessively expand beyond an expansion limit of material, thereby avoiding damage to the pressure relief diaphragm 6.

Figure 6:
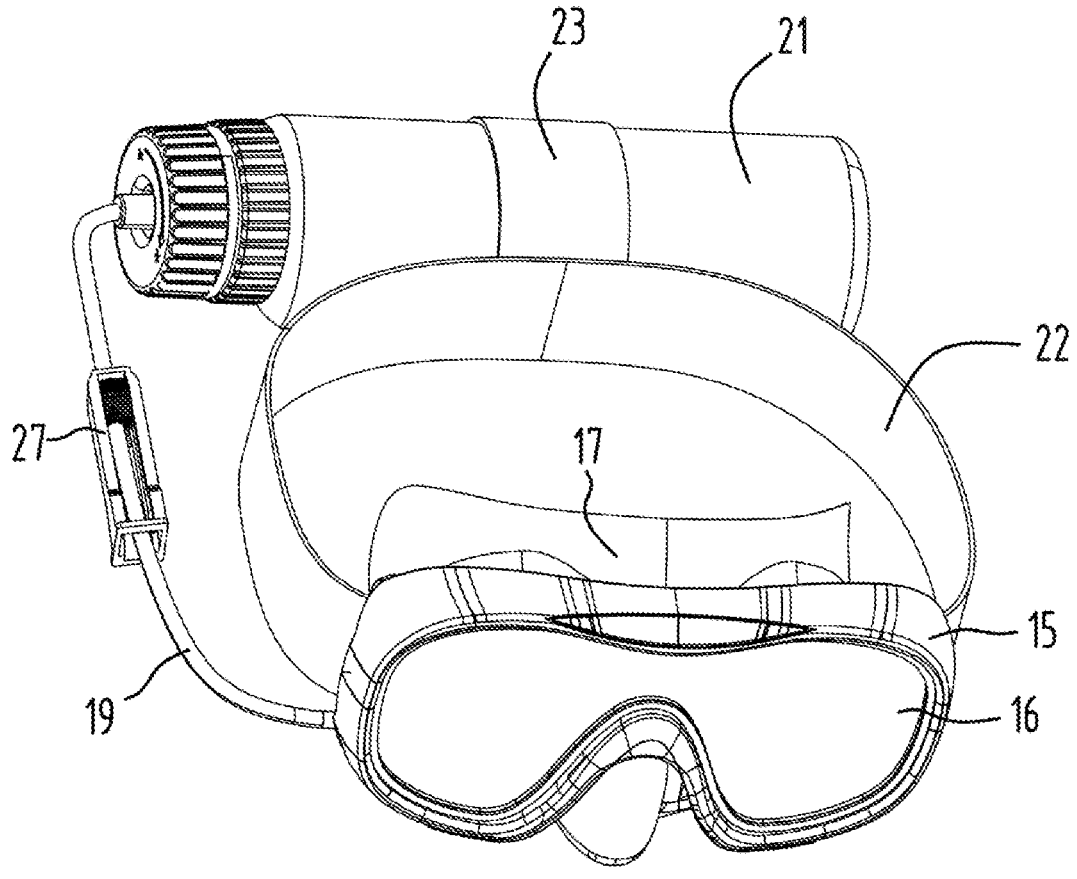
FIG. 6 is an entire front view of oxygen inhalation goggles according to the present invention.
Figure 7:
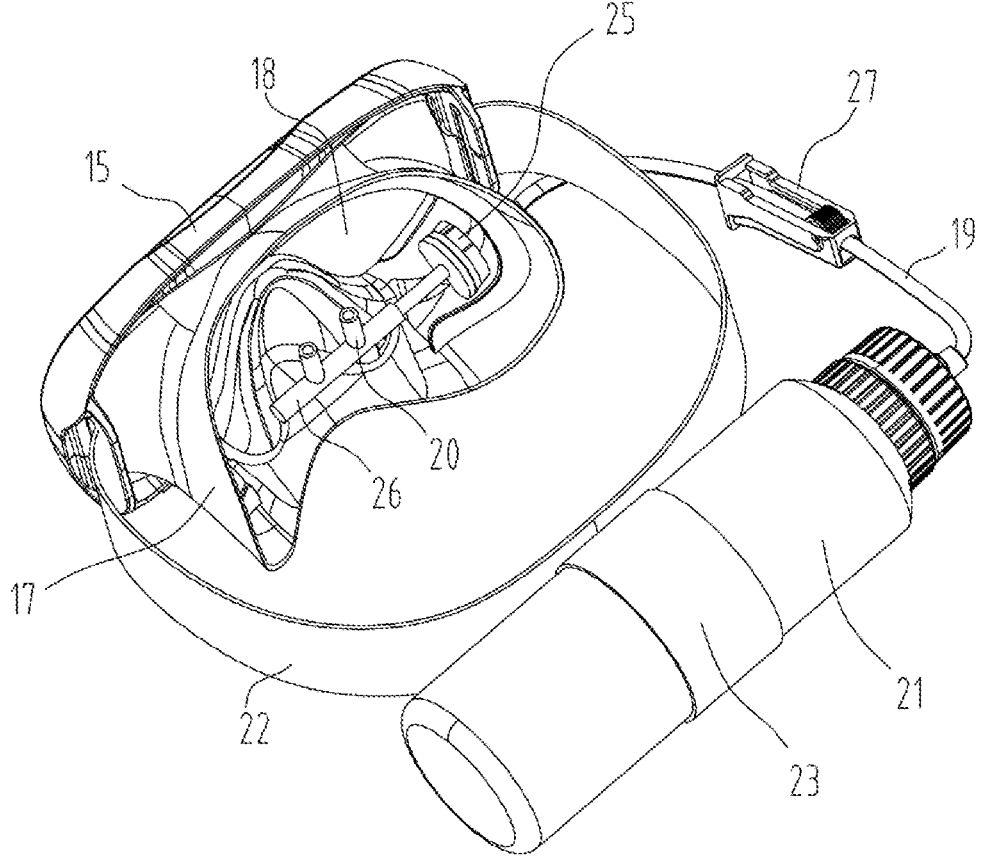
FIG. 7 is an entire rear view of oxygen inhalation goggles according to the present invention.

As shown in FIGS. 6 and 7, the oxygen inhalation goggles comprise a goggle frame 15, a flexible skirt edge 17, an inlet gas tube 19, a binding strap 22 and a portable oxygen cylinder 21. The goggle frame 15 is fitted with visual lenses 16 and a sealing strip is disposed between the goggle frame 15 and the lenses 16 to prevent water leakage. The flexible skirt edge 17 is disposed around the goggle frame 15 to form a respiratory chamber 18. The flexible skirt edge 17 is usually made of a rubber material. The respiratory chamber 18 comprises chambers of a nose part and an eye part. The visual lenses 16 are located at the position of the eye part and the chamber of the nose part protrudes outwardly to adapt to the shape of the nose part. It is noted that an annular sealing surface is disposed on an inner wall of the flexible skirt edge 17 and runs one circle along the peripheries of the eye part and the nose part, except for the position of the nostrils, i.e. the unreachable position between the nostrils and the mouth. In order to avoid discomfort, an end of the sealing surface facing toward the face part gradually becomes smaller toward the other end, such that the entire sealing surface is tilted forward to adapt to a face curve. When the flexible skirt edge 17 is attached to the face part, the sealing surface has the effect of enhancing the sealing. The sealing effect of the sealing surface is superior to that of the sealing ring or sealing strip especially for a curved surface structure like the face part.

One end of the inlet gas tube 19 is connected with the respirator chamber 18 and communicated with the respiratory chamber 18. The end of the inlet gas tube 19 penetrates through the flexible skirt edge 17 and extends to the position of the nose part. The end is provided with nose plugs 20 for inhalation. The other end of the inlet gas tube 19 is connected to the portable oxygen cylinder 21. Oxygen coming from the portable oxygen cylinder 21 runs through the inlet gas tube 19 and enters the nostrils through the nose plugs 20. In the embodiment, when the goggles are to be used, the inlet gas tube 19 is directly inserted into a gas discharge port of the portable oxygen cylinder 21. When an end of the inlet gas tube 19 is pressed into the gas discharge port of the portable oxygen cylinder 21, the gas discharge port of the portable oxygen cylinder 21 is in a normally-opened state. In this case, oxygen in the portable oxygen cylinder 21 enters the inlet gas tube 19 and then is opened, closed and adjusted by a regulator 27 so as to allow the oxygen to enter the respiratory chamber 18.

Figure 8:
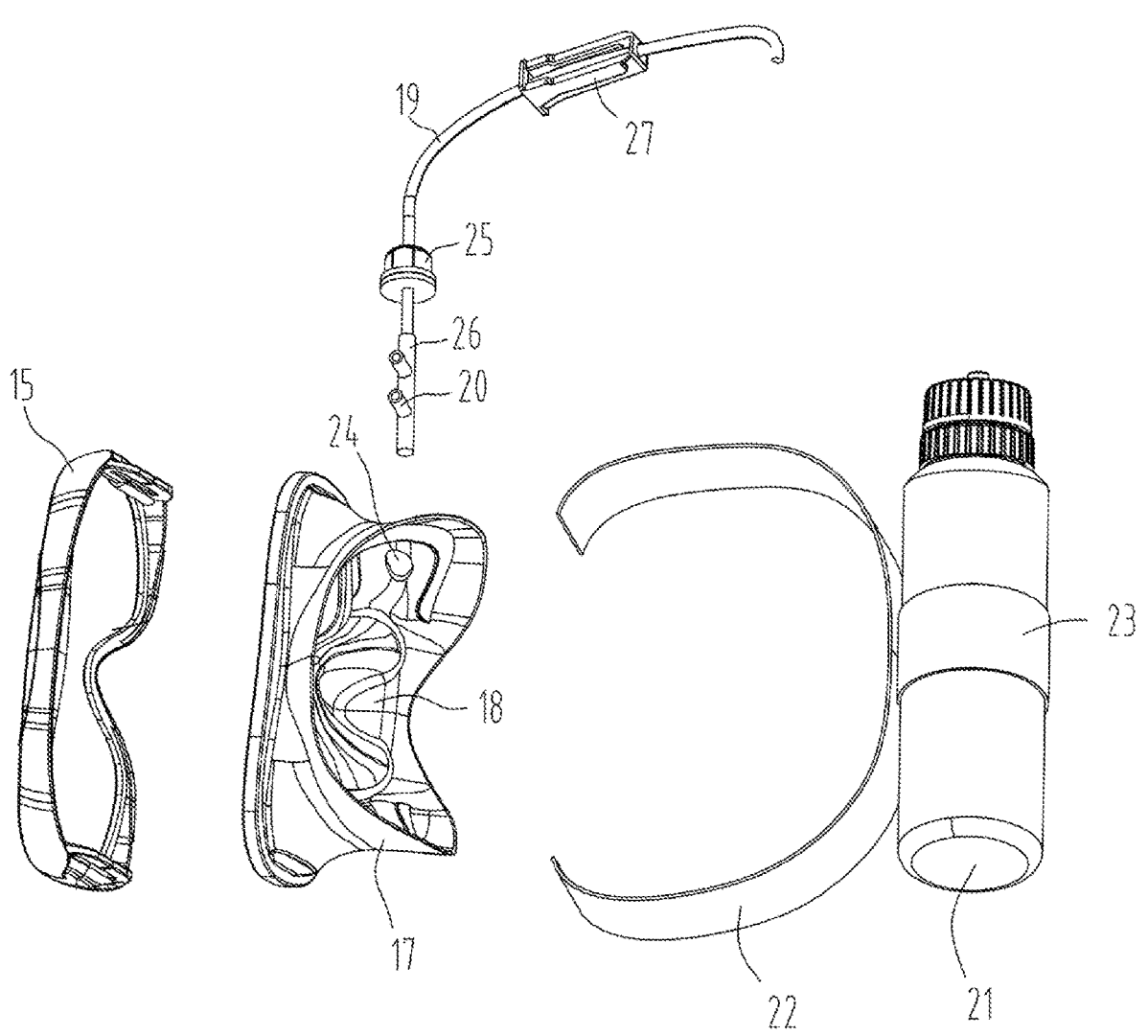
FIG. 8 is an entire exploded view of oxygen inhalation goggles according to the present invention.

As shown in FIG. 8, a through hole 24 is opened in the flexible skirt edge 17 and a rubber plug is mounted in the through hole 24. An end of the inlet gas tube 19 penetrates through the rubber plug 25 to communicate with the respiratory chamber 18 and extend to the nose part. A sealing ring for sealing is disposed between the rubber plug 25 and the through hole 24. Furthermore, a part of the inlet gas tube 19 passing through the rubber plug 25 is a straight line section to help the inlet gas tube 19 to pass through the rubber plug 25 and reduce the risk of gas leakage.

It is noted that, an extension portion 26 is disposed between the end of the inlet gas tube 19 and the nose plugs 20, and the extension portion 26 can be rotatably connected to the end of the inlet gas tube 19, that is, the extension portion 26 is sleeved on the end of the inlet gas tube 19. In this embodiment, the extension portion 26 is sleeved on the end of the inlet gas tube 19 and gas holes are opened on the extension portion 26. The nose plugs 20 are fixed on the extension portion 26 and connected with the gas holes. As the extension portion 26 rotates along the end of the inlet gas tube 19, the nose plugs 20 also rotate, helping to adjust an angle of the nose plugs 20 in the nostrils and satisfying different needs.

It is noted that, the sealing surface runs one circle along the peripheries of the eye part and the nose part except for the position of the nostrils, i.e. the unreachable position between the nostrils and the mouth. Such design can not only maintain comfort but also prevent interference with the end of the inlet gas tube 19 and the nose plugs 20 on the end. Further, the sealing surface can press the upper lip of the mouth part due to small region between the nostrils and the mouth.

The goggle frame 15 is provided with a binding strap 22 which is fixed to a head part to put on the goggles. In this embodiment, the binding strap 22 is an elastic fabric strap. The fabric strap has stretchability and width, which helps to securely sleeve and fix the fabric strap on the head part without using any auxiliary clips. Further, redundant length is not required for making length adjustment, which is favorable for the carrying and foldable storage. Due to its elasticity, the fabric strap is smaller in length than a non-elastic fabric strap. Thus, the binding strap has the advantages of material saving and smaller volume and thus is applicable to first aid supplies.

An elastic strap 23 is fixed on the binding strap 22. Both ends of the elastic strap 23 are connected to the binding strap 22 to form a ring shape into which the portable oxygen cylinder 21 is sleeved. The elastic strap 23 has elasticity which enables the elastic strap 23 to have stretchability. Thus, the elastic strap 23 can fix the portable oxygen cylinder 21.

Furthermore, the elastic strap 23 is located at a middle position of a length direction of the binding strap 22, that is, located behind the head part. When the portable oxygen cylinder 21 is sleeved into the elastic strap 23, the portable oxygen cylinder 23 is horizontally disposed relative to the binding strap 22 and the gas discharge port of the portable oxygen cylinder 21 is disposed at the same side as the through hole 24 on the flexible skirt edge 17. In this case, the length of the inlet gas tube 19 is shortened as possible. The through hole 24 and the gas discharge port of the portable oxygen cylinder 21 are disposed at a same horizontal level to effectively avoid gas leakage of both ends of the inlet gas tube 19. The inlet gas tube 19 is usually made of hose which is easy to fold. Even in a case of deformation, gas can run smoothly through the inlet gas tube 19. In addition, the through hole 24 of the flexible skirt edge 17 is opened at a side surface of the flexible skirt edge 17, i.e. at a cheek part.

In another embodiment, the elastic strap 23 may be located at a position of the binding strap 22 close to the goggle frame 15, that is, located above an ear part. When the portable oxygen cylinder 21 is sleeved into the elastic strap 23, the portable oxygen cylinder 21 is disposed horizontally relative to the binding strap 22. At this time, the portable oxygen cylinder 21 is located above the ear part and the gas discharge port is close to the goggle frame 15. In this way, the gas discharge port of the portable oxygen cylinder 21 and the inlet gas tube 19 are connected at a same side such that the length of the inlet gas tube 19 is minimized.

Furthermore, a width size of the elastic strap 23 is greater than or equal to ¼ of a body length of the portable oxygen cylinder 21. This design aims to prevent the portable oxygen cylinder 21 from tilting back and forth and reinforce the fixing of the portable oxygen cylinder 21.

The inlet gas tube 19 is provided with a regulator 27 for regulating a flow rate. The regulator 27 can serve as an inlet gas control switch as well as adjusting an inlet gas amount, which is similar to a flow rate regulator 27 on an infusion tube. Therefore, it is effective and easy to carry.

The binding strap 22 has stretchability such that the goggle frame 15 can be stably fixed onto the head part directly without using any auxiliary clips. Thus, the binding strap 22 can be quickly and easily operated. Further, the volume of the binding strap can be reduced to facilitate carrying.

Figure 9:
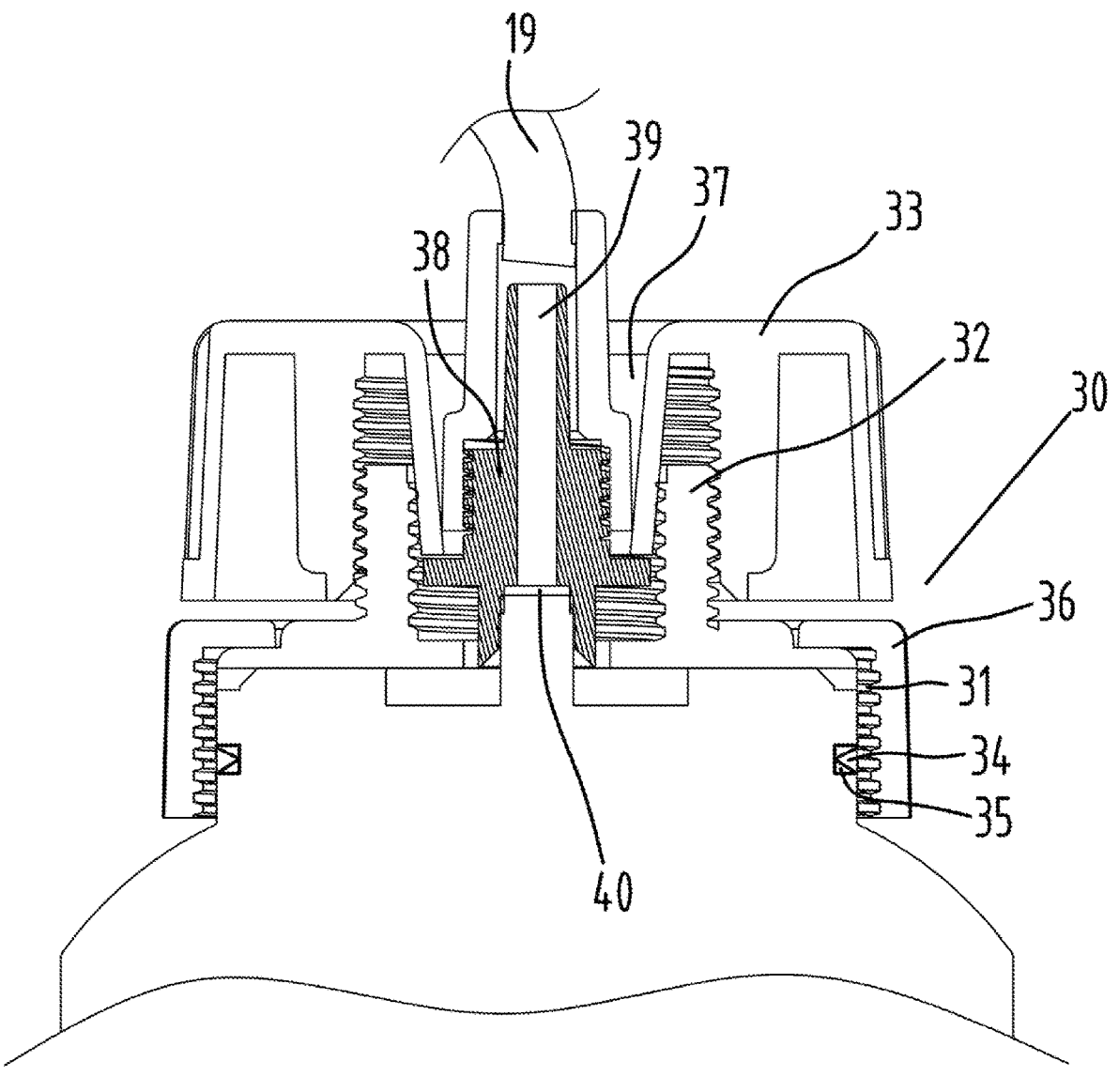
FIG. 9 is a sectional view of connection of an inlet gas tube and a portable oxygen cylinder according to the present invention.

As shown in FIG. 9, the inlet gas tube 19 is connected with the gas outlet end of the portable oxygen cylinder 21 through a first connection piece 30. The first connection piece 30 comprises a third connection portion 31, a fourth connection portion 32 and a fixing portion 33. A first protrusion 34 matching a first flare 35 of the gas outlet end of the portable oxygen cylinder 21 is disposed on an inner wall of the third connection portion 31. A first external hooping piece 36 is sleeved on an outer wall of the third connection portion 31 and the first external hooping piece 36 is connected with the outer wall of the third connection portion 31 by thread connection. The first external hooping piece 36 tightly embraces the third connection portion 31 onto the gas outlet end of the portable oxygen cylinder 21. A limiting port 37 is disposed upwardly on a fourth connection portion 32 and a fixing portion 33 is sleeved on the limiting port 37 and thread-connected with the limiting port 37. A limiting hole for allowing the inlet gas tube 19 to run through is opened in the center of the fixing portion 33. One end of the limiting hole is provided with a clip for clamping the port of the inlet gas tube 19 and the other end of the limiting hole is connected with a pressing portion 38 by thread connection. An outlet gas channel 39 connected with the limiting hole is opened on the pressing portion 38. A second limiting groove 40 is opened at an end of the outlet gas channel 39 facing toward the gas outlet end of the portable oxygen cylinder 21. The gas outlet of the gas outlet end of the portable oxygen cylinder 21 is inserted into the second limiting groove 40 and is abutted against a bottom surface of the second limiting groove 40, such that the gas outlet of the gas outlet end of the portable oxygen cylinder 21 is in an opened state, enabling oxygen therein to enter the inlet gas tube 19 through the outlet gas channel 39.

Figure 11:
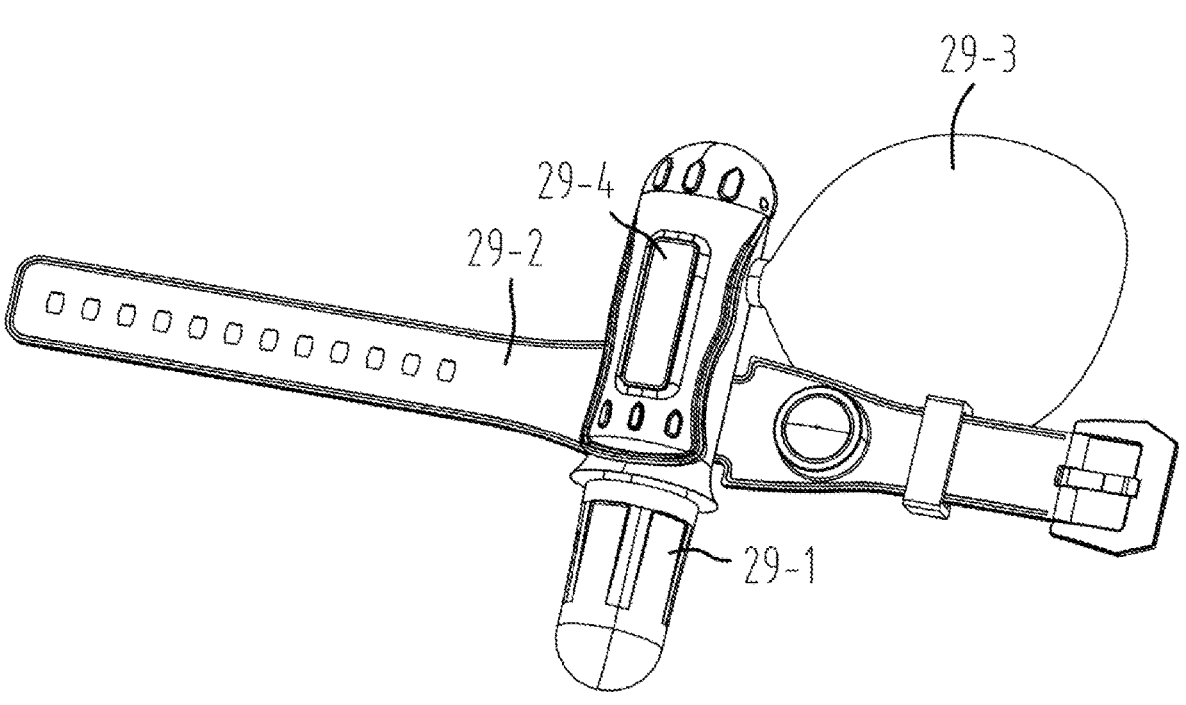
FIG. 11 is a structural schematic diagram illustrating a first aid bracelet.

Moreover, as shown in FIG. 11, the first aid bracelet 29 comprises a compressed gas storage tank 29-1, a wristband 29-2, a foldable airbag 29-3, and a control valve 29-4. A lateral hole is opened on the compressed gas storage tank 29-1, and the wristband 29-2 is inserted through the lateral hole to enable the compressed gas storage tank 29-1 to be fixed on the wristband 29-2. The foldable airbag 29-3 is foldably fixed on the wristband 29-2 through a strip. A gas inlet of the foldable airbag 29-3 is communicated with the compressed gas storage tank 29-1 through the control valve 29-4. When a person drowns in water, it is only required to open a switch of the control valve 29-4 on the wristband 29-2 to allow the compressed gas (mainly carbon dioxide) in the compressed gas storage tank 29-1 to quickly enter the foldable airbag 29-3 through the control valve 29-4. As the compressed gas enters, the foldable airbag 29-3 is inflated and quickly expanded to produce a buoyancy greater than a body weight of the person. The foldable airbag 29-3 pulls the wrist of the human body through the wristband 29-2 to float up to water surface.

The floating rope is made of high strength lightweight fibers and can float on water surface.

Figure 10:
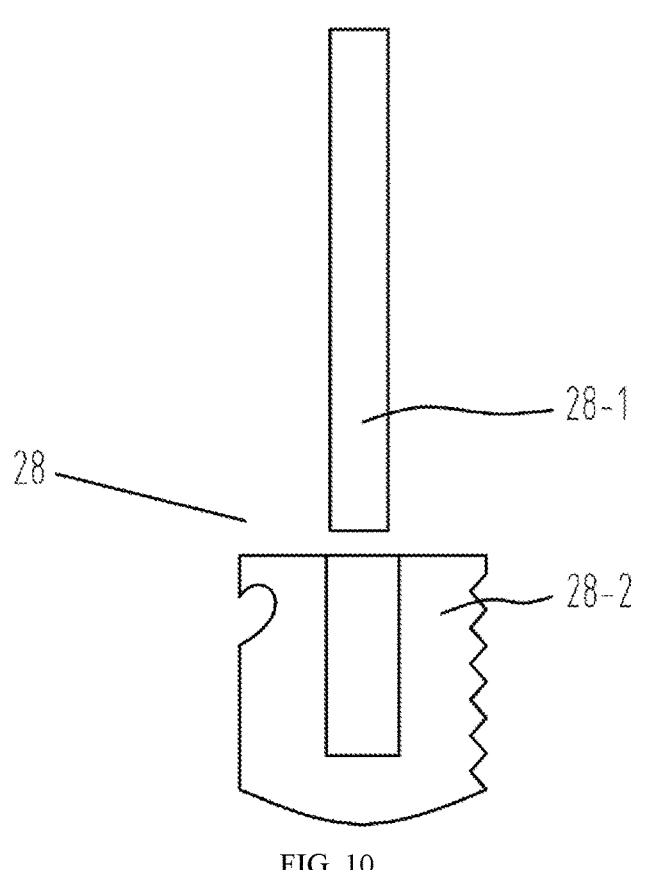
FIG. 10 is a structural schematic diagram illustrating a military shovel.

As shown in FIG. 10, the military shovel 28 comprises a handle 28-1 and a shovel 28-2. Saw teeth are disposed at an edge of a side of the shovel 28-2 and a cutting edge for sharp processing is disposed at an edge of the other side. A notch is further opened at the edge of the cutting edge, where an inner hook is formed in the notch. The top of the shovel 28-2 is shaped to be convex in middle and smoothly concave at both sides, so as to form a pointed top. The handle 28-1 and the shovel 28-2 are thread-connected to realize detachable mounting. Therefore, the military shovel 28 features small volume and high strength and can be used in the outdoor applications such as digging, sawing, hacking, piercing, cutting, gripping, covering and hooking etc.

The cut-resistant gloves are made of a polyester material. A steel wire net layer is disposed in the cut-resistant gloves to increase a strength and a toughness of the cut-resistant gloves and prevent skin injury due to a pointed object cutting the gloves.

The multifunctional tool bag comprises a working lamp, a safety hammer, a flashlight, a headlamp and an emergency urine bag. The working lamp has the functions of warning and emergency charge. The safety hammer can break a window. The flashlight and the headlamp can be used for illumination. The emergency urine bag is used for temporary urine storage.

The medical supply bag comprises gauzes, adhesive bandages, iodine cotton swabs and adhesive tapes to perform emergency treatment for skin injuries.

In the descriptions of the present invention, it is understood that orientations or positional relationships indicated by the terms such as "upper", "lower", "front", "rear" "left", "right", "vertical", "horizontal", "top", "bottom", "inside" and "outside" are based on the orientation or positional relationship shown in accompanying drawings and used only for ease of descriptions and simplification of descriptions and not to indicate or imply that the indicated devices or elements must have a particular orientation, or be constructed or operated in a particular orientation. Therefore, such terms shall not be understood as limiting of the present invention.

In the present invention, unless otherwise clearly stated or defined, the terms "mount", "connect", "couple", and "fix" and the like shall be understood in a broad sense, for example, may be fixed connection, or detachable connection, or formed into one piece; or may be mechanical connection, or electrical connection; or direct connection or indirect connection through an intermediate medium, or may be internal communication between two elements or mutual interaction of two elements. Those skilled in the art may understand the specific meanings of the above terms in the present invention according to actual situations.

In the present invention, unless otherwise clearly stated or defined, the first feature being "on" or "below" the second feature refers to that the first feature and the second feature are in direct contact, or the first feature and the second feature are in indirect contact through an intermediate medium. Furthermore, the first feature being "above" or "on" the second feature refers to that the first feature is exactly above or obliquely above the second feature, or only refers to that the first feature has a higher horizontal height than the second feature. The first feature being "under" or "below" the second feature refers to that the first feature is exactly under or obliquely below the second feature, or only refers to that the first feature has a smaller horizontal height than the second feature. Finally, it is to be pointed out that the above embodiments are merely used to describe the technical solution of the present invention rather than limit the present invention. Although detailed descriptions are made to the present invention by referring to the preceding embodiments, those skilled in the art should understand that the technical solutions recorded in the above embodiments may be modified or part or all of technical features thereof may be equivalently substituted. Such modifications or substitutions will not cause the essences of the corresponding technical solutions to depart from the spirits and scopes of the technical solutions of various embodiments of the present invention.

What is claimed is:

1. A vehicle-carried first aid kit, comprising: a portable respirator, oxygen inhalation goggles, a first aid bracelet (29), and a military shovel (28), wherein the portable respirator comprises a main valve body (1) and a gas cylinder (2); a pressure relief diaphragm (6) is mounted inside the main valve body (1); an outer side of the pressure relief diaphragm (6) is in communication with an atmospheric environment and an inner side of the pressure relief diaphragm (6) forms a low-pressure compartment (7) with an inner wall of the main valve body (1); the low-pressure compartment (7) is in communication with a gas outlet (2-1) of a gas outlet end of the gas cylinder (2) through an inlet gas channel (3); a pressure relief valve (8) is disposed inside the main valve body (1); a pressure relief channel (8-1) in communication with the inlet gas channel (3) and the low-pressure compartment (7) is disposed in a valve body (8-2) of the pressure relief valve (8); a pressure relief opening (8-3) is disposed on the valve body (8-2) of the pressure relief valve (8); the pressure relief diaphragm (6) is linked with the pressure relief valve (8) through a pressing mechanism(9); the main valve body (1) is provided with an inflation opening (12) in communication with the inlet gas channel (3) and the main valve body (1) is provided with a mouthpiece interface (13) in communication with the low-pressure compartment (7); an exhaust opening (11) in communication with the low-pressure compartment (7) is disposed at the bottom of the main valve body (1), and the exhaust opening (11) is provided with a one-way exhaust diaphragm;

wherein the oxygen inhalation goggles comprise a goggle frame (15) fitted with lenses (16) and a flexible skirt edge (17) disposed around the goggle frame (15) to form a respiratory chamber (18); an inlet gas tube (19) is inserted into the flexible skirt edge (17); a first end of the inlet gas tube (19) communicates with the respiratory chamber (18) and extends to a nose part, and the first end of the inlet gas tube (19) is provided with nose plugs (20) for ease of inhalation; a second end of the inlet gas tube (19) is connected with a portable oxygen cylinder (21); the goggle frame (15) is provided with a binding strap (22) fixed to a head part, and the binding strap (22) is provided with an elastic strap (23) for detachably mounting the portable oxygen cylinder (21) to the binding strap (22); and wherein a gas inlet end of the inlet gas channel (3) is connected with the gas outlet end of the gas cylinder (2) through a connection piece (4); the connection piece (4) includes a first connection portion (4-1) and a second connection portion (4-2); protruding blocks (4-3) matching a flare (2-2) of the gas outlet end of the gas cylinder (2) is disposed on an inner wall of the first connection portion (4-1); an external hooping piece (4-4) is sleeved on an outer wall of the first connection portion (4-1); the external hooping piece (4-4) tightly embraces the first connection portion (4-1) onto the gas outlet end of the gas cylinder (2); the second connection portion (4-2) is slidably connected with an input end of the inlet gas channel (3); a first limiting groove (3-1) in communication with the inlet gas channel (3) is provided at the center of the input end of the inlet gas channel (3); the first limiting groove (3-1) has an inner diameter greater than an inner diameter of the inlet gas channel (3), thereby forming an annular shoulder surface at a transition from the first limiting groove (3-1) to the inlet gas channel (3); the gas outlet (2-1) of the gas outlet end of the gas cylinder (2) extends into the first limiting groove (3-1); a gap is reserved between the annular shoulder surface and an end surface of the gas outlet (2-1); when the second connection portion (4-2) slides toward the inlet gas channel (3), the annular shoulder surface is abutted and pressed against the end surface of the gas outlet (2-1), so as to open the gas outlet (2-1); when the second connection portion (4-2) slides away from the inlet gas channel (3), the annular shoulder surface goes away from the end surface of the gas outlet (2-1) of the gas cylinder (2), so as to close the gas outlet (2-1).

2. The vehicle-carried first aid kit of claim 1, wherein the top of the main valve body (1) is provided with a detachable end cover (10), and a surface of the detachable end cover (10) is provided with an air vent; the outer side of the pressure relief diaphragm (6) is in communication with the atmospheric environment through the air vent.

3. The vehicle-carried first aid kit of claim 1, wherein the pressing mechanism (9) includes a movable lever (9-1) and a push rod (9-2); one end of the movable lever (9-1) is abutted against the pressure relief diaphragm (6) and the other end of the movable lever (9-1) is connected with the piston (8-4) of the pressure relief valve (8) through the push rod (9-2); a first end of the piston (8-4) is abutted inside the valve body (8-2) through an elastic piece (8-5), and a second end of the piston (8-4) is abutted against an outlet of the pressure relief channel (8-1) through a plug (8-6).

4. The vehicle-carried first aid kit of claim 1, wherein a through hole (24) is opened in the flexible skirt edge (17) and a rubber plug (25) is mounted in the through hole (24) an end of the inlet gas tube (19) penetrates through the rubber plug (25) to communicate with the respiratory chamber (18) and extend to the nose part; a part of the inlet gas tube (19) passing through the rubber plug (25) is a straight line section.

5. The vehicle-carried first aid kit of claim 4, wherein an end of the inlet gas tube (19) is rotatably connected with an extension portion (26), and the nose plugs (20) are fixed on the extension portion (26).

6. The vehicle-carried first aid kit of claim 1, wherein both ends of the elastic strap (23) are connected with the binding strap (22) to form a ring shape and the portable oxygen cylinder (21) is sleeved into the ring-shaped elastic strap (23).

7. The vehicle-carried first aid kit of claim 6, wherein the elastic strap (23) is located in a middle position of a length direction of the binding strap (22) and the portable oxygen cylinder (21) is horizontally fixed; a gas discharge port of the portable oxygen cylinder (21) is disposed at the same side as the through hole (24) of the flexible skirt edge (17).

8. The vehicle-carried first aid kit of claim 7, wherein a width size of the elastic strap (23) is greater than or equal to ¼ of a body length of the portable oxygen cylinder (21).

9. The vehicle-carried first aid kit of claim 1, wherein the multi-functional tool bag includes a working lamp, a safety hammer, a flashlight, a headlamp and an emergency urine bag, and the medical supply bag includes gauzes, adhesive bandages, iodine cotton swabs and adhesive tapes.

* * * * *